(12) United States Patent
Isobayashi et al.

(10) Patent No.: US 11,493,491 B2
(45) Date of Patent: Nov. 8, 2022

(54) CHEMICAL SENSOR AND METHOD FOR DETECTING TARGET SUBSTANCE

(71) Applicant: KABUSHIKI KAISHA TOSHIBA, Minato-ku (JP)

(72) Inventors: Atsunobu Isobayashi, Yokohama (JP); Yoshiaki Sugizaki, Fujisawa (JP); Sadato Hongo, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 814 days.

(21) Appl. No.: 16/352,579

(22) Filed: Mar. 13, 2019

(65) Prior Publication Data

US 2020/0080977 A1   Mar. 12, 2020

(30) Foreign Application Priority Data

Sep. 12, 2018   (JP) ............................. JP2018-170654

(51) Int. Cl.
| | | |
|---|---|---|
| G01N 33/00 | (2006.01) | |
| G01N 1/40 | (2006.01) | |
| G01N 27/40 | (2006.01) | |
| G01N 27/414 | (2006.01) | |

(52) U.S. Cl.
CPC ....... *G01N 33/0031* (2013.01); *G01N 1/4005* (2013.01); *G01N 27/40* (2013.01); *G01N 33/0036* (2013.01); *G01N 33/0062* (2013.01); *G01N 2333/72* (2013.01)

(58) Field of Classification Search
CPC .......... G01N 33/0031; G01N 33/0036; G01N 33/0062; G01N 1/4005; G01N 27/40; G01N 27/4145; G01N 27/4146; G01N 2333/726
See application file for complete search history.

(56) References Cited

U.S. PATENT DOCUMENTS

| | | |
|---|---|---|
| 2002/0132273 A1 | 9/2002 | Stryer et al. |
| 2002/0132289 A1 | 9/2002 | Clement et al. |
| 2002/0168692 A1 | 11/2002 | Cass |
| 2002/0177168 A1 | 11/2002 | Ikematsu |
| 2003/0017618 A1 | 1/2003 | Ikematsu |
| 2003/0045472 A1 | 3/2003 | Axel et al. |
| 2005/0074817 A1 | 4/2005 | Lin et al. |

(Continued)

FOREIGN PATENT DOCUMENTS

| | | |
|---|---|---|
| JP | 2010-243301 A | 10/2010 |
| WO | WO 2009/096304 A1 | 8/2009 |
| WO | WO 2018/116186 A1 | 6/2018 |

OTHER PUBLICATIONS

Park et al. "Ultrasensitive Flexible Graphene Based Field-Effect Transistor (FET)-Type Bioelectronic Nose." (2012) 12 5082-5090. (Year: 2012).*

(Continued)

*Primary Examiner* — Christopher Adam Hixson
(74) *Attorney, Agent, or Firm* — Oblon, McClelland, Maier & Neustadt, L.L.P.

(57) ABSTRACT

A chemical sensor for detecting a target substance in a gas sample, including a membrane; and an olfactory receptor fragment which is fixed to the membrane. The chemical sensor optionally includes a source electrode connected to one end of the membrane; and a drain electrode connected to the other end of the membrane, in which the membrane is a graphene.

16 Claims, 5 Drawing Sheets

Specification includes a Sequence Listing.

(56) References Cited

U.S. PATENT DOCUMENTS

| | | |
|---|---|---|
| 2007/0054266 A1 | 3/2007 | Sato et al. |
| 2010/0248268 A1 | 9/2010 | Woods et al. |
| 2011/0008212 A1 | 1/2011 | Ichimura |
| 2011/0059544 A1 | 3/2011 | Hong et al. |
| 2014/0364330 A1 | 12/2014 | Mershin et al. |
| 2015/0065363 A1 | 3/2015 | Johnson, Jr. et al. |
| 2016/0122832 A1 | 5/2016 | Peralta-Yahya et al. |
| 2017/0242004 A1 | 8/2017 | Hanson et al. |
| 2017/0299602 A1 | 10/2017 | Johnson, Jr. et al. |

OTHER PUBLICATIONS

Pelosi et al. "Odorant-Binding Proteins as Sensing Elements for Odour Monitoring." (2018) 18 3248. (Year: 2018).*

Takashi Matsuo, "Odorant-binding Proteins and Evolution of Host-plant Preference in Insects", Protein, Nucleic Acid and Enzyme (vol. 52, No. 15), 2007, pp. 1980-1986 ((with machine translation).

Mamiko Ozaki et al., "Chemosensory Stimulant Carrier Proteins in Insect Olfactory and Gustatory Receptors", Protein. Nucleic Acid and Enzyme (vol. 53. No. 2). 2008, pp. 111-118 (with machine translation).

* cited by examiner

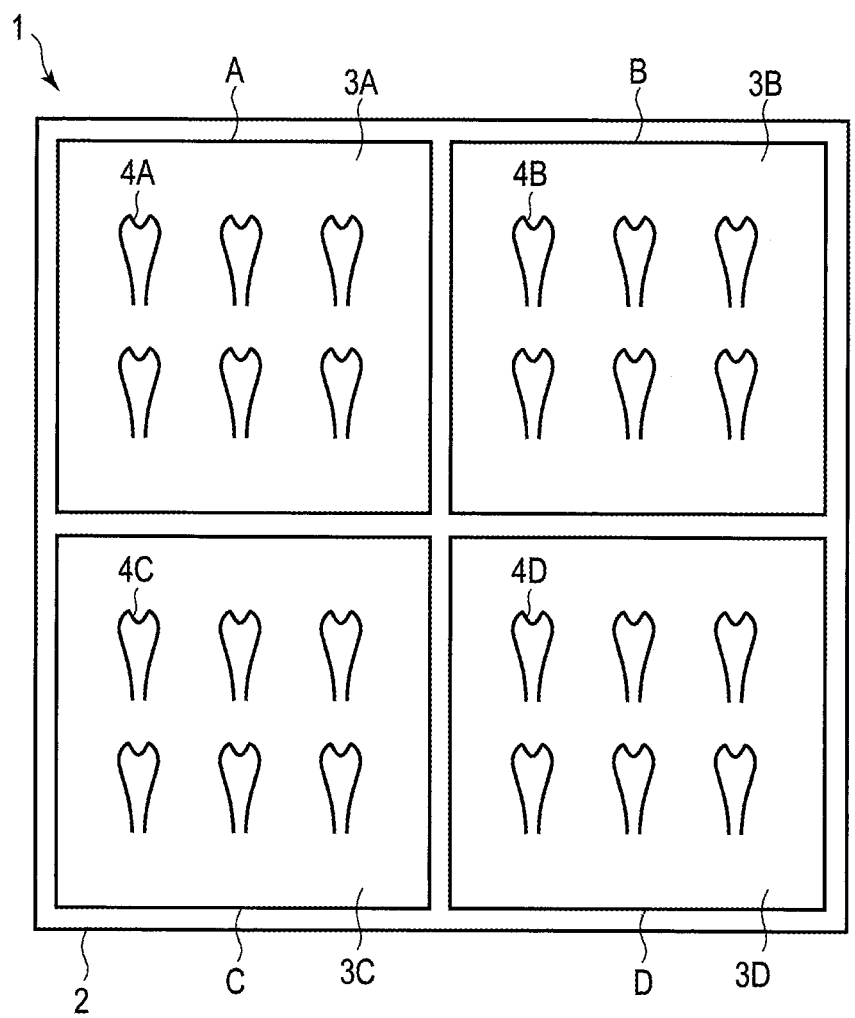
F I G. 3

CHEMICAL SENSOR AND METHOD FOR DETECTING TARGET SUBSTANCE

CROSS-REFERENCE TO RELATED APPLICATIONS

This application is based upon and claims the benefit of priority from Japanese Patent Application No. 2018-170654, filed Sep. 12, 2018, the entire contents of which are incorporated herein by reference.

FIELD

Embodiments described herein relate generally to a chemical sensor and a method for detecting a target substance.

BACKGROUND

Humans have five senses of sight, hearing, touch, taste, and smell. Among the five senses, for senses that can be replaced by physical sensing, artificial devices corresponding to them have been developed, for example, sight can be replaced by a camera, hearing can be replaced by a microphone, and touch can be replaced by a pressure sensor. In recent years, also for taste, a membrane potential sensor and the like using an artificial lipid membrane have been put into practical use. On the other hand, an olfactory sensor lags behind in terms of both sensor sensitivity and portability.

For example, it is considered that detection of substances which can be detected by the sense of smell of an animal (hereinafter, referred to as "odorants") is useful in the fields of detecting biological information and detecting harmful substances in the air.

For example, as a chemical sensor for the odorants, a chemical sensor using a metal oxide or a conductive polymer as a sensitive membrane has been reported. In such a chemical sensor, the presence of the odorants is trying to be detected by changing the physical properties of the sensitive membrane by nonspecific adsorption of a plurality of odorants into the sensitive membrane, and leaning patterns of such a change are learned as a specific odor. However, by the means of this method, it is difficult to specifically detect the odor substances with high sensitivity.

Under such circumstances, there is a need for a chemical sensor which can specifically detect odorants in a gas sample with high sensitivity.

BRIEF DESCRIPTION OF THE DRAWINGS

FIG. 3 shows a diagram of the chemical sensor according to an embodiment.

DETAILED DESCRIPTION

In general, according to one embodiment, a chemical sensor includes a membrane and olfactory receptor fragments fixed to one surface of the membrane.

According to another embodiment, there is provided a chemical sensor in which instead of the olfactory receptor fragments, target substance transporting carriers are fixed to a surface of a membrane. According to still another embodiment, there are provided a kit including a chemical sensor, and a method for detecting a target substance using a chemical sensor.

Hereinafter, various embodiments will be described with reference to the drawings. Each drawing is a schematic view for promoting understanding of embodiments, and shapes, dimensions, ratios, and the like thereof are different from actual ones. However, these drawings are appropriately changed in design in consideration of the following description and known techniques.

Hereinafter, the chemical sensor, the chemical sensor kit, and the method for detecting a target substance will be described.

First Embodiment

Chemical Sensor

Figure 1:
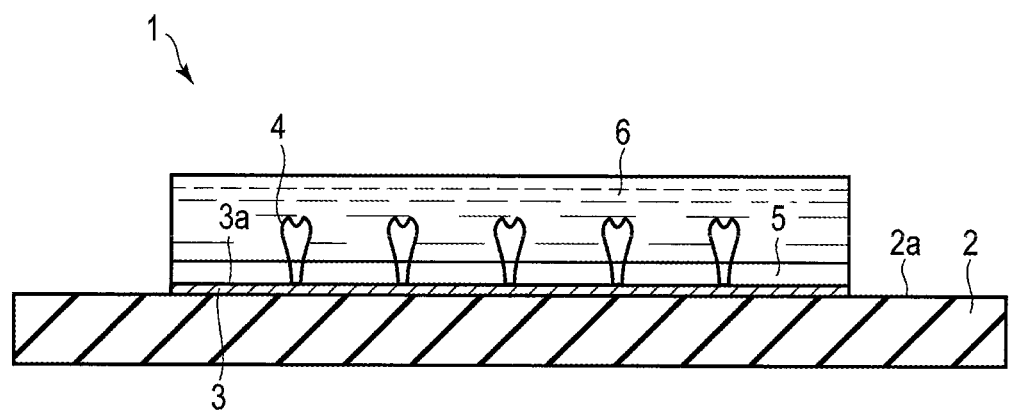
FIG. 1 shows a diagram of a chemical sensor according to an embodiment.

FIG. 1 shows a cross-sectional view of an example of a chemical sensor according to a first embodiment.

A chemical sensor 1 includes a substrate 2 and a sensitive membrane 3 which is sensitive to a target substance. The sensitive membrane 3 is disposed on a surface 2a of the substrate 2. On a surface 3a of the sensitive membrane 3 opposite to the substrate 2, olfactory receptor fragments 4 are fixed. In addition, the surface 3a is coated with a blocking agent 5. The olfactory receptor fragment 4 is coated with a liquid phase 6 provided on the sensitive membrane 3.

Hereinafter, each configuration will be described in detail.

The substrate 2 has, for example, a rectangular plate shape. A material of the substrate 2 is, for example, silicon, glass, ceramics, a polymer material, or the like. A size of the substrate 2 is not limited, but can be, for example, 100 mm×10 mm×1 mm (width×length×thickness) and the like.

The sensitive membrane 3 is made of a substance whose physical properties, for example, electric resistance is changed when a structure, a state of electric charge, or the like of the substance binding to the sensitive membrane 3 is changed. The sensitive membrane 3 is made of conductors such as a polymer, gold (Au), silver (Ag), copper (Cu), nickel (Ni), silicon (Si), silicide or the like, or two-dimensional materials such as graphene, carbon nanotube, molybdenum disulfide ($MoS_2$) or tungsten diselenide ($WSe_2$), or the like. The sensitive membrane 3 has, for example, a shape of a single or multiple membranes or nanowires. The substrate 2 and the sensitive membrane 3 are configured, for example, as a part of a detector (not shown) that converts the change in physical properties of the sensitive membrane 3 into an electrical signal.

The olfactory receptor fragment 4 is a fragment of an olfactory receptor. The olfactory receptor is a kind of G protein-coupled receptors expressed in olfactory cells (olfactory receptor neuron) of olfactory organs of animals. The olfactory receptor is a transmembrane protein, which serves to activate the G protein present in a cell when odorants bind to ligand binding sites thereof present extracellularly.

The olfactory receptor fragment 4 is a fragment containing a sequence of sites contained in the olfactory receptors, which specifically bind to target substances. For example, such sequence contains ligand binding sites located extracellularly of the olfactory receptor. The olfactory receptor fragment 4 can be prepared, for example, by obtaining an amino acid sequence of the ligand binding sites from a database of the olfactory receptor and synthesizing oligopeptides having the amino acid sequence. However, the olfactory receptor fragment 4 is simply required to specifically be capable of binding to the target substance. Therefore, the olfactory receptor fragment 4 may be, for example, one in which the sequence of the ligand binding sites is partially modified, or one in which a new sequence is added. It is preferable that the olfactory receptor fragment 4 is, for example, a fragment of 5 to 20 amino acids. For example, the olfactory receptor fragment 4 may further contain a linker or a scaffold, and in this case, the olfactory receptor fragment 4 may have a length of 10 to 30 amino acids.

For example, as the olfactory receptor, one which is expressed in an animal can be used. An animal is, for example, a vertebrate, an insect, or the like. For example, an olfactory receptor of human, fly, mosquito, mouse, rat, rabbit, ox, or dog can be used.

For example, when the target substance is a musk type perfume, as the olfactory receptor fragment 4, sequence MLSNLLQEQQTITFVGCII (sequence No. 1) of the ligand binding sites of human olfactory receptor (muscone receptor) OR5AN1 can be used. Alternatively, sequence CGSNVIRHFFC (sequence No. 2) can be used.

The fact that the olfactory receptor fragment 4 is fixed to the sensitive membrane 3 means that the olfactory receptor fragment 4 binds to the sensitive membrane 3. For example, the olfactory receptor fragment 4 can be fixed to the sensitive membrane 3 by adding a modifying group to the olfactory receptor fragment 4 and/or the sensitive membrane 3 and chemically synthesizing them. For example, it is preferable that the olfactory receptor fragments 4 are disposed on the sensitive membrane 3 at equal intervals, for example, in 1 to 3 per 10 nm$^2$.

The blocking agent 5 is disposed, for example, so as to coat the surface 3a. As the blocking agent 5, for example, metal oxides ($Al_2O_3$, $HfO_2$, and the like), proteins, organic molecules, lipid membranes, peptides, or the like can be used. By providing such a blocking agent 5, it is possible to prevent substances which are not targets contained in the gas sample (contaminants), from binding to the surface of the sensitive membrane 3. However, the blocking agent 5 may be used if necessary, and it is not necessary to use the blocking agent 5 when it is assumed that the detection is performed under a condition with few contaminants.

The liquid phase 6 is disposed on the sensitive membrane 3 and is a liquid coating the olfactory receptor fragment 4. The liquid phase 6 is, for example, water, physiological saline, an ionic liquid, or an organic solvent such as a PB buffer, a PBS buffer, DMSO, or alcohol, any mixture thereof, or the like. The liquid phase 6 can prevent the olfactory receptor fragment 4 from degenerating or being damaged due to drying. The liquid phase 6 also serves as a medium to transport the target substance from the gas sample to the olfactory receptor fragment 4. For example, a thickness of the liquid phase 6 is preferably greater than 0 µm and equal to or smaller than 50 µm. By making the thickness of the liquid phase 6 equal to or smaller than 50 µm, a target substance 12 can reach the olfactory receptor fragment 4 in a short time and can be detected more efficiently.

Figure 2:
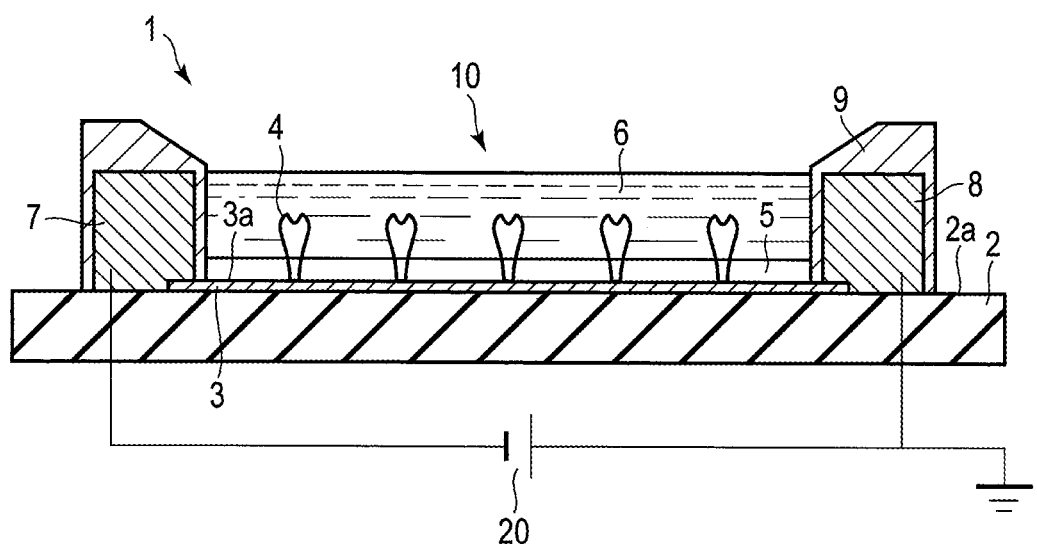
FIG. 2 shows a diagram of the chemical sensor according to an embodiment.

For example, the chemical sensor may have a configuration of a graphene field effect transistor (hereinafter, also referred to as "graphene FET"). An example of such a chemical sensor is shown in FIG. 2.

The chemical sensor 1 in this example includes the substrate 2 having the insulating surface 2a and the sensitive membrane 3 of graphene disposed on the surface 2a. The olfactory receptor fragments 4 are fixed to the surface 3a of the sensitive membrane 3 opposite to the substrate 2. In addition, the surface 3a is coated with a blocking agent 5. The olfactory receptor fragment 4 is coated with the liquid phase 6. Further, a source electrode 7 is connected to one end of the sensitive membrane 3, and a drain electrode 8 is connected to the other end thereof. A DC power supply 20 is connected to the source electrode 7 and the drain electrode 8. In addition, a wall portion 9 made of an insulating material is erected from the surface of the substrate 2 and the sensitive membrane 3. The wall portion 9 surrounds a peripheral edge of the sensitive membrane 3 when viewing the chemical sensor 1 in a plan view and covers outer peripheral surfaces of the source electrode 7 and the drain electrode 8. By the wall portion 9, a well 10 having the sensitive membrane 3 as a bottom part is formed.

For example, the source electrode 7 and the drain electrode 8 are configured so that, when a source-drain voltage ($V_{sd}$) is applied from the DC power supply 20, a source-drain current ($I_{sd}$) flows from the source electrode 7 to the drain electrode 8 via the sensitive membrane 3. At this time, the sensitive membrane 3 of graphene functions as a channel for the source electrode 7 and the drain electrode 8. A circuit connecting each member may be formed in the substrate 2.

For example, the substrate 2 has an insulating film disposed on the surface 2a on the side of the sensitive membrane 3. The insulating film is, for example, silicon oxide, silicon nitride, aluminum oxide, a polymer material, a self-assembled monolayer of organic molecules, or the like. The substrate 2 may include an insulating film provided on the surface 2a side and a layer of a conductor functioning as a gate electrode. In this case, it is preferable that a thickness of an insulator is as thin as possible within a range not to damage insulating properties. For example, it is preferable to set the thickness of the insulator to be about several nm. Such a thin film can be formed by, for example, an atomic layer deposition (ALD) method.

In this example, the sensitive membrane 3 is a monolayer graphene film having a thickness corresponding to one carbon atom. The graphene film may be provided in plural layers. The size of the sensitive membrane 3 is not limited, but it can be set to be, for example, 0.1 to 500 µm×0.1 to 500 µm (width×length). Practically, the sensitive membrane is easily manufactured as long as it is 10 to 100 µm×10 to 100 µm.

Examples of materials of the source electrode 7 and the drain electrode 8 may include metal such as gold (Au), silver (Ag), copper (Cu), palladium (Pd), platinum (Pt), nickel (Ni), titanium (Ti), chromium (Cr) or aluminum (Al), or conductive substances such as zinc oxide (ZnO), indium tin oxide (ITO), IGZO, and a conductive polymer.

Examples of the insulating materials of the wall portion 9 may include polymer substances such as an acrylic resin, a polyimide, a polybenzoxazole, an epoxy resin, a phenol resin, a polydimethylsiloxane, or a fluororesin, or an inorganic insulating film made of silicon oxide, silicon nitride, or indium tin oxide, or the like, the self-assembled monolayer of organic molecules, or the like can be used. The well 10 has a liquid-tight structure.

The chemical sensor 1 may be configured to further include the gate electrode (not shown) connected to the liquid phase 6. In that case, the thickness of the insulating film provided on the substrate 2 may be several nm or more.

According to the chemical sensor 1 having the configuration of the graphene FET described above, it is possible to detect the change in the electric resistance of the graphene (channel) which is the sensitive membrane 3 as the change in the source-drain current value. Such a chemical sensor 1 can be manufactured by a semiconductor process.

The chemical sensor is not limited to the graphene FET, but may have a configuration of another charge detection element, such as a surface plasmon resonance element (SPR), a surface acoustic wave (SAW) element, a film bulk acoustic resonator (FEAR) element, a quartz crystal microbalance (QCM) element, a MEMS cantilever element, or the like.

Hereinafter, one unit including the substrate 2, the sensitive membrane 3, one type of olfactory receptor fragment 4, and the liquid phase 6 is referred to as "sensor element". In another embodiment, plural types of sensor elements can be mounted on one chemical sensor. Each of the plural types of sensor elements is provided with different types of olfactory receptor fragments 4, and it is possible to detect different types of target substances.

The chemical sensor including the plural types of sensor elements will be described with reference to FIG. 3.

The chemical sensor 1 in this example has a sensor element A including a sensitive membrane 3A to which an olfactory receptor fragment 4A is fixed, a sensor element B including a sensitive membrane 3B to which an olfactory receptor fragment 4B is fixed, a sensor element C including a sensitive membrane 3C to which an olfactory receptor fragment 4C is fixed, and a sensor element D including a sensitive element 3D to which an olfactory receptor fragment 4D is fixed. Each of the sensitive membranes 3A to 3D is configured so as to be able to individually detect a change in physical properties thereof.

The number, type, arrangement, and the like of sensor elements mounted on one chemical sensor 1 are not limited to those shown in FIG. 3. For example, it is preferable that the number of sensor elements mounted on one chemical sensor is 1 or more and 1000 or less. It is preferable that the type of sensor elements is one or more and 10 or less. Further, each of the types of chemical sensor elements may be provided in plural.

Method for Detecting a Target Substance

Hereinafter, the method for detecting a target substance using the chemical sensor according to the first embodiment will be described. The detection method is a method for detecting a target substance in a gas sample.

The gas sample is, for example, a gas which can contain a target substance. The gas sample is, for example, air, expiration, another gas generated from an analysis target such as a living body or an object, air around an analysis target, or the like.

The target substance is a target to be analyzed by the detection method. The target substance is, for example, a substance contained in a gas, which can be a ligand of an olfactory receptor of an animal. The target substance is, for example, a volatile organic compound (VOC), and are, for example, odorants, pheromone substances, or the like. The target substance is, for example, alcohols, esters, aldehydes, or the like but is not limited thereto. The target substance is, for example, a hydrophobic substance.

Figure 4:
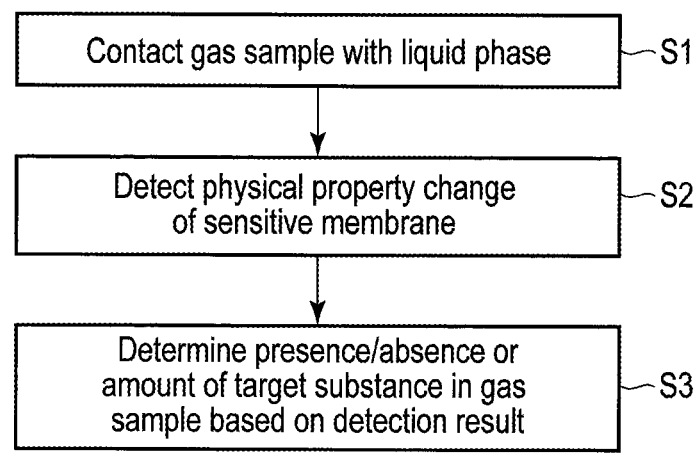
FIG. 4 shows a flowchart of a method for detecting a target substance according to an embodiment.

FIG. 4 is a diagram showing a schematic flow of an example of the method for detecting a target substance according to the first embodiment.

The method for detecting a target substance includes, for example, the following processes: (S1) bringing the gas sample into contact with the liquid phase of the sensor according to the first embodiment, (S2) detecting the physical property change of the sensitive membrane, and (S3) determining the presence/absence or the amount of target substance in the gas sample based on the detection result.

Hereinafter, a principle of detecting odorants by performing each of the above processes will be described.

Figure 5:
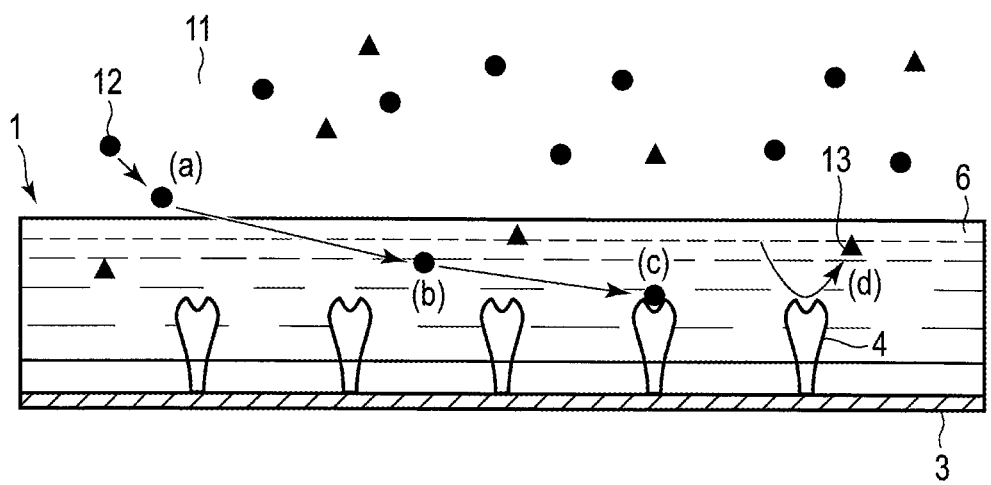
FIG. 5 shows a schematic view of a state when the chemical sensor according to an embodiment is used.

In the process (S1), a gas sample 11 comes into contact with the liquid phase 6 of the chemical sensor 1. The state of the chemical sensor 1 at this time is shown in FIG. 5. By the contact of the gas sample 11 with the liquid phase 6, the target substance 12 contained in the gas sample 11 incorporated into the liquid phase 6 from the interface of the liquid phase 6 ((a) and (b) of FIG. 5), and binds to the olfactory receptor fragment 4 ((c) of FIG. 5). By this binding, the physical properties of the sensitive membrane 3 are changed. The physical properties are, for example, the electric resistance or the like of the sensitive membrane 3.

On the other hand, since the olfactory receptor fragment 4 specifically binds to the target substance 12, the non-target substance (contaminant 13) does not bind to the olfactory receptor fragment 4 ((d) of FIG. 5). Therefore, it is possible to prevent the contaminant 13 from affecting the physical property change of the sensitive membrane 3.

In the process (S2), the physical property change of the sensitive membrane 3 is detected as the electrical signal change. For example, this detection can be performed by a member which is connected to the sensitive membrane 3 and converts the physical property change thereof into the electrical signal change. The electrical signal is, for example, a current value, a potential value, an electric capacitance value, an impedance value, or the like. The electrical signal change is, for example, an increase, a decrease, or a disappearance in the electrical signal, a change in an integrated value within a specific time, or the like. In the case of using the graphene FET described above, the physical property change can be detected as a change in a current value between the source and the drain.

In the process (S3), the presence/absence or amount of target substance in the gas sample is determined based on the detection result. For example, when the electrical signal changes, it may be determined that the target substance 12 is present in the gas sample 11, and when there is no the electrical signal change, it may be determined that the target substance 12 is not present. In addition, when the electrical signal is changed greater than a preset threshold value, it may be determined that the target substance 12 is present, and when the electrical signal is changed smaller than the threshold value, it may be determined that the target substance 12 is not present. Such a threshold value can be obtained by, for example, analyzing the gas sample known as containing the target substance by the chemical sensor to obtain the change value of the electrical signal.

Alternatively, the amount of target substance may be determined according to the change amount of the electrical signal. In this case, the amount of target substance may be determined by preparing a calibration curve of the change amount with respect to the concentration of the target substance using the target substance whose concentration is known in advance and comparing the target substance with the prepared calibration curve.

By the processes described above, the target substance in the gas sample can be specifically detected with high sensitivity.

The method for detecting a target substance may be performed by a device which automatically performs each process. Such a device includes, for example, the chemical sensor 1, a liquid feeding section which feeds a liquid, a reagent or the like for forming the liquid phase 6 onto the sensitive membrane 3 of the chemical sensor 1, a sample introduction section which brings the gas sample 11 into contact with the liquid phase 6 of the chemical sensor 1, a detection section which converts the physical property change of the sensitive membrane 3 into the electrical signal change, and a data processing section which stores and processes the information on the electric signal obtained from the detection section, and a control section which controls the operation of each of these sections. The operations of the above processes (S1) to (S3) may be executed by an operator's input of the device, or may be executed by a program included in the control section.

The conventional methods of detecting odorants have attempted to specify an odor by non-specifically adsorbing a plurality of odorants into a sensitive membrane and then associating obtained patterns of data of changes in physical properties of the sensitive membrane with a specific odor. In this method, a steady state of compositions of the odorants is defined in advance, and it is only determined whether there is the odorants which are the same as or different from the steady state pattern. Therefore, for example, when the target odor is detected in the changing environment or when many odorants are increased or decreased from the steady state, and thus, it was difficult to identify the type of detected odorants.

On the other hand, according to the chemical sensor and the method for detecting a target substance of the embodiment, since the olfactory receptor fragment which specifically binds to the target substance is used, even under the condition that the compositions of the substances contained in the gas are changed, it is possible to prevent the non-target substances (contaminants) from affecting the detection. Therefore, it is possible to detect the target substance with extremely high accuracy and high sensitivity.

In addition, conventionally, in the method for detecting a target substance using a protein such as a receptor, there is a problem that activity is lost due to a change in a three-dimensional structure of the protein over time. As a result, the detection sensitivity is lowered. In addition, there is a further problem in that the transmembrane protein was unable to maintain the three-dimensional structure under the condition without biological membrane. As a result, the activity thereof is likely to be lost.

On the contrary, in the chemical sensor according to the embodiment, for example, an olfactory receptor fragment of 5 to 20 amino acids is used. As a result, it is possible to prevent the activity from being lowered due to the change in the three-dimensional structure and enable molecules capturing the target substance to be stably present on the sensitive membrane while maintaining the activity as the receptor. Therefore, it is possible to stably perform the detection over a long period of time.

In addition, since the chemical sensor according to the embodiment includes the liquid phase 6, the olfactory receptor fragment 4 is protected from the degeneration or the like due to drying. Therefore, the stable detection can be performed.

The method for detecting a target substance in the case where the chemical sensor includes plural types of chemical sensor elements will be described with reference to the example of FIG. 3.

In such a method for detecting a target substance, the above processes (S1) and (S2) are similarly performed using the chemical sensor 1 of FIG. 3. In the process (S2), the electrical signal is individually obtained from each sensor element A to D. In the process (S3), based on the type (the type of olfactory receptor fragments fixed thereto) and the number of sensor elements in which the electrical signal changes, a type of target substance mixtures containing a plurality of target substances may be specified. For example, it can be determined that when the electrical signal changes in the sensor elements A and B, a target substance mixture I is present in the gas sample, or when the electrical signal changes in the sensor elements A, C, and D, a target substance mixture II is present in the gas sample, and the like.

Alternatively, in the chemical sensor including a plurality of each of the sensor elements, depending on the ratio of the number of the sensor elements A, B, C, and D in which the signals changes, the presence or absence of a specific target substance mixture may be determined. That is, it is possible to specify the type of target substance mixtures contained in the gas sample by the ratio.

The target substance mixture is a mixture in which a plurality of target substances is mixed in a specific combination. For example, one target substance mixture is associated with one specific "odor", and the presence/absence or amount of "odor" may be determined by the above method. In addition, "odor" can be associated with a cause of giving off "odor" in advance, and the cause of giving off odor can be specified by such detection.

In another embodiment, in the method for detecting a target substance, the target substance transporting carrier can be used. The target substance transporting carrier transports the target substance 12 from the gas sample 11 to the olfactory receptor fragment 4 via the liquid phase 6. In this method, before the process (S2), adding the target substance transporting carrier to the liquid phase 6 is further included.

The target substance transporting carrier is a pocket-like substance having a hydrophilic part on an outer side thereof and hydrophobic part on an inner side thereof. Since the hydrophobic part opens outwardly, the target substance transporting carrier can incorporate the hydrophobic target substance into the hydrophobic part. The behavior of the target substance when the target substance transporting carrier is used will be described with reference to FIG. 6.

Figure 6:
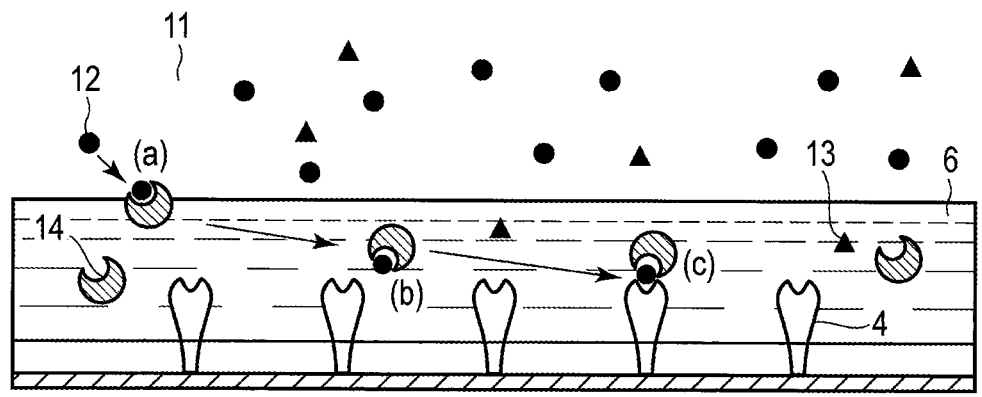
FIG. 6 shows a schematic view of the state when the chemical sensor according to an embodiment is used.

As shown in FIG. 6, the target substance 12 in the gas sample 11 binds to the hydrophobic part of the target substance transporting carrier 14 at the interface of the liquid phase 6 ((a) of FIG. 6) and is incorporated into the liquid phase 6 ((b) of FIG. 6). When the target substance 12 is transported to the vicinity of the olfactory receptor fragment 4, the target substance 12 is released from the target substance transporting carrier 14 and binds to the olfactory receptor fragment 4 ((c) of FIG. 6). By using the target substance transporting carrier 14, for example, the hydrophobic target substance 12 is more efficiently incorporated into the liquid phase 6 and transported to the olfactory receptor fragment 4, therefore the target substance 12 can be more quickly detected with high sensitivity.

The target substance transporting carrier 14 is, for example, an odorant binding protein (OBP) expressed in an olfactory organ of an animal. There is a report that in a mucosa of the olfactory organ, the OBP incorporates odorants into the hydrophobic part and transported to the olfactory receptor. For example, as the OBP, OBP2a (human), OBP1 (pig), OBP57 (fly), OBP3 (aphid) can be used. The type of OBP used is selected according to the type of target substance 12. For example, the OBP may also incorporate the target substance 12 selectively or specifically.

Alternatively, the target substance transporting carrier 14 may be an inclusion compound such as cyclodextrin. For example, the cyclodextrin is a compound which has a hydrophilic part on an outside thereof and a hollow hydrophobic part on an inside thereof. It is known that in an aqueous solution, the cyclodextrin incorporate the hydrophobic compound and gradually release the compound with time. Such an inclusion compound can also be used for detecting the target substance 12 in which the corresponding OBP is not found.

The concentration of the target substance transporting carrier 14 in the liquid phase 6 is preferably 1 nM to 1 mM, for example.

In addition, the target substance transporting carrier 14 tends to bind to the target substance under a neutral condition and is easy to release the target substance under an acidic condition. Therefore, by setting the vicinity of the olfactory receptor fragment 4 to be the acidic condition, the target substance transporting carrier 14 can easily release the target substance 12, and the target substance 12 can be detected with higher sensitivity.

Therefore, for example, it is preferable that the olfactory receptor fragment 4 is a peptide containing an amino acid having a low isoelectric point. For example, it is preferable to use peptides containing more glutamic acid and aspartic acid, and containing less lysine, arginine, and histidine. In addition, it is preferable that the blocking agent 5 is an acidic substance. For example, as the acidic blocking agent 5, a peptide using an amino acid having a low isoelectric point, a sugar chain at the sialic acid terminal, an acidic phospholipid, for example, a phospholipid not modified with choline, a substance modified with a COOH group or an $SO_3H$ group, a compound having albumin or an acidic group, or the like can be used. Alternatively, the blocking agent such as Prevelex A modified with an acidic group may also be used. Alternatively, by positively charging the substrate 2, cations may be reduced and anions may be increased around the olfactory receptor fragment 4.

In another embodiment, the method for detecting a target substance may include a refresh process. Such a method further includes, after the process (S4), adding an enzyme to the liquid phase 6, wherein the enzyme decomposes the target substance, removing the liquid phase 6, and providing the fresh liquid phase on the sensitive membrane.

When the enzyme is added to the liquid phase 6, the target substance 12 binding to the olfactory receptor fragment 4 and the target substance 12 contained in the liquid phase 6 are decomposed by the enzyme. Next, a new liquid phase 6 is fed onto the sensitive membrane 3, and an old liquid phase 6 containing decomposition products and an enzyme is extruded and discharged. As a result, the chemical sensor can be used for the next analysis.

The enzyme which decomposes the target substance is, for example, an enzyme which decomposes the odorant expressed in the olfactory organ of an animal. As the enzyme, for example, aldehyde oxidase, glutathione-S-transferase, cytochrome P450, or the like can be used.

The enzyme is preferably contained in the liquid phase at a concentration of 1 nM to 1 mM. Also, after adding the enzyme, it is preferable to leave the target substance, for example, for 5 to 30 minutes in order to sufficiently decompose the target substance.

Conventionally, in the analysis using the reaction between the receptor and the ligand, since the receptor and the ligand are strongly binding to each other and hardly separated. Therefore, in many cases, the sensor cannot be used for the next analysis and is discarded. However, by performing such a refresh process using the enzyme which decomposes the target substance, it is possible to repeatedly use the chemical sensor for the plurality of analyzes. Therefore, it is unnecessary to disassemble or discard the sensor every analysis, which is economical.

Second Embodiment

Chemical Sensor

Figure 7:
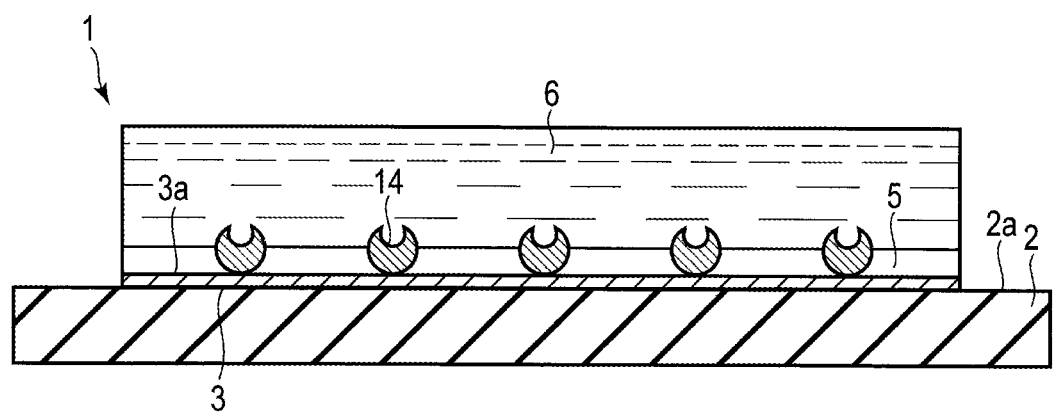
FIG. 7 shows a diagram of the chemical sensor according to an embodiment.

FIG. 7 is a diagram showing an example of a chemical sensor according to a second embodiment.

A chemical sensor 1 includes a substrate 2 having a surface 2a and a sensitive membrane 3 disposed on the surface 2a. Target substance transporting carriers 14 are fixed to a surface 3a of the sensitive membrane 3 on a side opposite to the substrate 2. In addition, the surface 3a is coated with a blocking agent 5. The target substance transporting carrier 14 is coated with a liquid phase 6 provided on the surface 3a.

In the chemical sensor 1 in this example, instead of the olfactory receptor fragment 4 of the chemical sensor according to the first embodiment, the target substance transporting carrier 14 is fixed to the sensitive membrane 3. Other configurations can be the same as those of the first chemical sensor.

As the target substance transporting carrier 14 to be fixed to the sensitive membrane 3, any one of the target substance transporting carriers 14 described above, which specifically incorporate the target substance 12, can be used. The target substance transporting carrier 14 can be fixed to the sensitive membrane 3 by adding a modification group to the target substance transporting carrier 14 and/or the sensitive membrane 3 and chemically synthesizing them.

The chemical sensor 1 according to the second embodiment may have a configuration of, similarly to the first embodiment, graphene FET, another charge detection element, a surface plasmon resonance element (SPR), a surface acoustic wave (SAW) element, a film bulk acoustic resonator (FEAR) element, a quartz crystal microbalance (QCM) element, a MEMS cantilever element, or the like.

Method for Detecting a Target Substance

Figure 8:
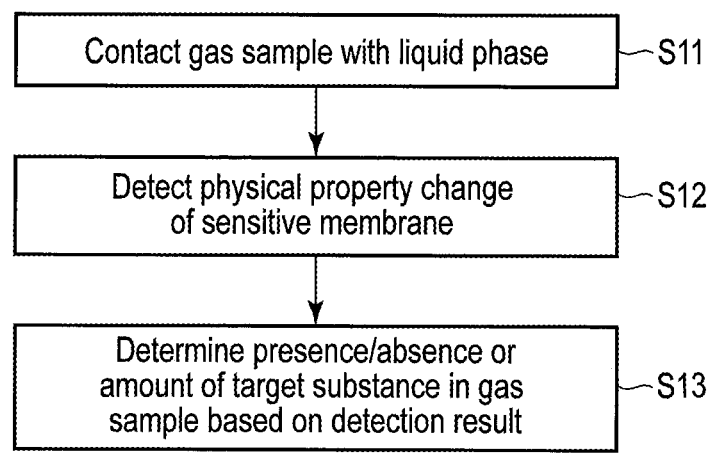
FIG. 8 shows a flowchart of the method for detecting a target substance according to an embodiment.

Hereinafter, a method for detecting a target substance using the chemical sensor according to the second embodiment will be described. FIG. 8 is a diagram showing a schematic flow of an example of the method for detecting a target substance according to the second embodiment.

The method for detecting a target substance includes, for example, the following processes: (S11) bringing the gas sample into contact with the liquid phase of the chemical sensor according to the second embodiment, (S12) detecting a change in physical properties of the sensitive membrane, and (S13) determining the presence/absence or the amount of target substance in the gas sample based on the detection result.

Figure 9:
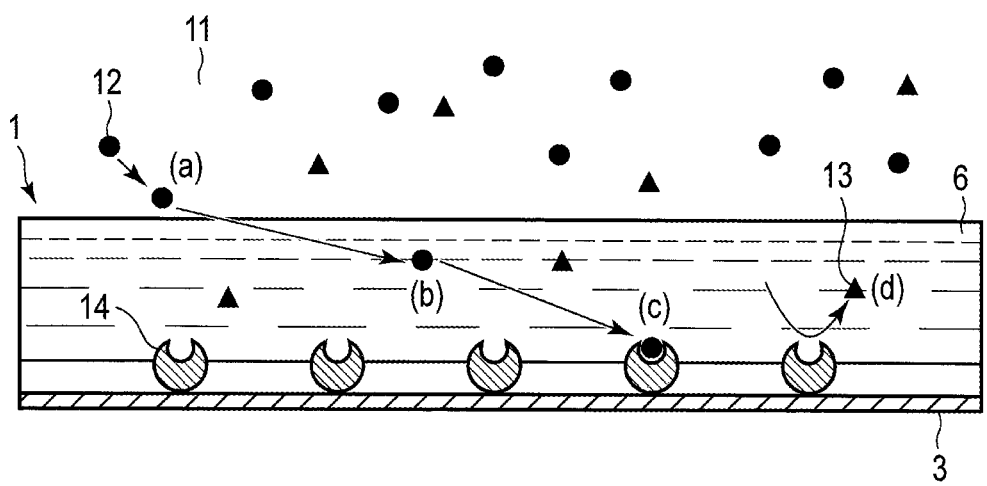
FIG. 9 shows a schematic view of the state when the chemical sensor according to an embodiment is used.

As the gas sample 11 used in the detection method, the same gas sample as one described in the first embodiment can be used. FIG. 9 shows the state of the chemical sensor 1 when the gas sample 11 comes into contact with the liquid phase 6 of the chemical sensor 1 in the process (S11). The target substance 12 incorporated into the liquid phase 6 by the contact of the gas sample 11 with the liquid phase 6 ((a) and (b) FIG. 9) and binds to the hydrophobic part of the target substance transporting carrier 14 ((c) of FIG. 9). The physical properties of the sensitive membrane 3 is changed due to the binding of the target substance 12 and the target substance transporting carrier 14 ((c) of FIG. 9), which can be detected as an electrical signal. On the other hand, contaminants 13 do not bind to the target substance transporting carriers 14 ((d) of FIG. 9).

The processes (S12) and (S13) can be carried out by the same method as the processes (S2) and (S3).

The target substance transporting carrier 14 has high binding ability with the target substance 12 when the target substance 12 is incorporated from the gas sample. In addition, in the method for detecting a target substance according to the second embodiment, the mechanism is simpler than using both the target substance transporting carrier and the olfactory receptor fragment. Therefore, according to the method of the second embodiment, it is expected that the reaction efficiency between the target substance 12 and the target substance transporting carrier 14 is increased and the detection time is shortened.

The target substance transporting carrier 14 is likely to bind to the target substance 12 under neutral to basic conditions. Therefore, by setting the vicinity of the target substance transporting carrier 14 to be neutrality to basicity, the target substance 12 can be detected with higher sensitivity. Therefore, it is preferable to use, for example, neutral to basic target substance transporting carriers 14. Such a target substance transporting carrier 14 may be, for example, an amino group and/or cyclodextrin modified with a trimethylammonio group. Alternatively, it is preferable to use a basic substance as the blocking agent 5. As the basic blocking agent 5, a compound containing a peptide containing a larger amount of amino acids with a high isoelectric point (for example, histidine, proline, threonine, isoleucine and the like), a basic lipid membrane such as a lipid bilayer membrane, or other basic groups can be used.

Here, when the phospholipid bilayer membrane is used as the blocking agent 5, by supplying flippase after the basic group of the phospholipid in the upper layer of the bilayer membrane is consumed by the detection of the target substance, it is possible to make an upper layer of the bilayer membrane into the basic state again by transferring to a lower layer of the bilayer membrane the phospholipid in which the basic group is consumed.

The detection method may further include a refresh process using the enzyme described in the first embodiment. In the refresh process, it is preferable to set the liquid phase 6 to be an acidic condition. As a result, the target substance transporting carrier 14 easily releases the target substance 12, and the refresh effect is enhanced. Alternatively, the refresh process may be performed by setting the liquid phase 6 to be the acidic condition without using the enzyme.

Chemical Sensor Kit

According to the first and second embodiments, a chemical sensor kit is also provided. The chemical sensor kit includes, for example, the following combinations:

(1) The chemical sensor and the target substance transporting carrier of the first embodiment;

(2) The chemical sensor and the enzyme of the first embodiment;

(3) The chemical sensor, the target substance transporting carrier, and the enzyme of the first embodiment; or (4) The chemical sensor and the enzyme of the second embodiment.

The target substance transporting carrier or the enzyme is contained in a kit in a state, for example, in which it is contained in a solvent, and is contained in a container. As the solvent, for example, an aqueous solution, an alcohol, an organic solvent or an ionic liquid can be used. As the container, for example, a poly container can be used.

In addition to these configurations, the kit may include other configurations such as a cleaning agent, a liquid constituting the liquid phase, an acid solution for adjusting pH and/or an alkaline solution and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A chemical sensor, comprising:
a membrane;
an olfactory receptor fragment which is fixed to the membrane;
a source electrode connected to one end of the membrane;
a drain electrode connected to the other end of the membrane;
a liquid phase which is provided on the membrane to coat the olfactory receptor fragment; and
a target substance transporting carrier contained in the liquid phase,
wherein
the membrane is a graphene, and
the target substance transporting carrier has a pocket-like shape having a hydrophilic part on an outer side and a hydrophobic part on an inner side.

2. The chemical sensor of claim 1, wherein a thickness of the liquid phase is greater than 0 μm and equal to or less than 50 μm.

3. The chemical sensor of claim 1, wherein the target substance transporting carrier is an odorant binding protein or an inclusion compound.

4. The chemical sensor of claim 1, further comprising:
a blocking agent provided on a surface of the membrane to which the olfactory receptor fragment is fixed.

5. The chemical sensor of claim 4, wherein the blocking agent is an acidic substance.

6. A chemical sensor, comprising:
an olfactory receptor fragment which is capable of binding to a target substance; and
a detector which detects a physical property change due to the binding of the target substance and the olfactory receptor fragment.

7. A chemical sensor, comprising:
a membrane; and
a target substance transporting carrier fixed to the membrane,
wherein the target substance transporting carrier has a pocket-like shape having a hydrophilic part on an outer side and a hydrophobic par on an inner side.

8. The chemical sensor of claim 7, further comprising:
a source electrode connected to one end of the membrane; and
a drain electrode connected to the other end of the membrane,
wherein the membrane is a graphene.

9. The chemical sensor of claim 7, further comprising:
a liquid phase which is provided on the membrane to coat the olfactory receptor fragment.

10. The chemical sensor of claim 9, wherein a thickness of the liquid phase is greater than 0 μm and equal to or less than 50 μm.

11. The chemical sensor of claim 7, further comprising:
a blocking agent provided on a surface of the membrane to which the target substance transporting carrier is fixed.

12. The chemical sensor of claim 11, wherein the blocking agent is a basic substance.

13. The chemical sensor of claim 7, wherein the target substance transporting carrier is an odorant binding protein or an inclusion compound.

14. A chemical sensor, comprising:
a target substance transporting carrier which has a pocket-like shape having a hydrophilic part on an outer side and a hydrophobic part on an inner side; and
a detector which detects a physical property change due to the binding of a target substance and the target substance transporting carrier.

15. The chemical sensor of claim 1, wherein a target substance to be detected by the chemical sensor is an odorant.

16. The chemical sensor of claim 1, wherein the membrane is a sensitive membrane to a target substance to be detected by the chemical sensor.

* * * * *

SEQUENCE LISTING

```
<160> NUMBER OF SEQ ID NOS: 2

<210> SEQ ID NO 1
<211> LENGTH: 19
<212> TYPE: PRT
<213> ORGANISM: human

<400> SEQUENCE: 1

Met Leu Ser Asn Leu Leu Gln Glu Gln Gln Thr Ile Thr Phe Val Gly
1               5                   10                  15

Cys Ile Ile

<210> SEQ ID NO 2
<211> LENGTH: 11
<212> TYPE: PRT
```

-continued

```
<213> ORGANISM: human

<400> SEQUENCE: 2

Cys Gly Ser Asn Val Ile Arg His Phe Phe Cys
1               5                   10
```